United States Patent [19]

Osborg

[11] Patent Number: 4,677,227
[45] Date of Patent: Jun. 30, 1987

[54] PROCESS FOR PREPARING HYDRAZINES

[75] Inventor: Hans Osborg, P.O. Box 152, 80 Long View Rd., Port Washington, N.Y. 11050

[73] Assignee: Hans Osborg, Port Washington, N.Y.

[21] Appl. No.: 691,506

[22] Filed: Jan. 14, 1985

Related U.S. Application Data

[62] Division of Ser. No. 370,980, Apr. 22, 1982.

[51] Int. Cl.$^4$ ............................................. C07C 135/00
[52] U.S. Cl. .................................... 564/118; 564/114; 564/117
[58] Field of Search .................... 564/118, 114, 117

[56] References Cited

U.S. PATENT DOCUMENTS 2,472,361  6/1949  Arsem .................................. 564/118

*Primary Examiner*—Charles F. Warren
*Assistant Examiner*—John A. Sopp
*Attorney, Agent, or Firm*—Dann, Dorfman, Herrell & Skillman

[57] ABSTRACT

Substantially anhydrous hydrocarbyl-substituted chloramine is efficiently prepared by reacting a primary or secondary amine with a chlorinating agent selected from hypochlorous acid or chlorine monoxide in a non-aqueous reaction medium, without co-production of an amine hydrochloride salt.

3 Claims, No Drawings

PROCESS FOR PREPARING HYDRAZINES

This is a division of application Ser. No. 370,980 filed Apr. 22, 1982.

BACKGROUND OF THE INVENTION

The present invention relates to an improved process for preparing hydrazine and various hydrocarbyl-substituted hydrazines.

Hydrazine, alkyl-substituted hydrazines, particularly unsymmetrical dimethylhydrazine (UDMH), and phenyl-substituted hydrazines, are important commercial compounds having a wide range of utilities, such as pharmaceuticals, fuels, agricultural products, intermediates in the preparation of blowing agents, and the like.

A number of processes have been used heretofore for the preparation of hydrazine and its derivatives. For example, the Raschig process is a commercial synthesis of hydrazine from chloramine and ammonia in aqueous solution. Intially, sodium hypochlorite is reacted with an excess of ammonia to form chloramine, with sodium hydroxide being produced as a by-product. The chloramine then reacts with ammonia to form hydrazine. In the first stage of the process, chloramine is formed rapidly. However, in the second stage the reaction of chloramine with ammonia is slow and requires heat for completion. The rate of formation of the hydrazine product increases with temperature. As a side reaction, the hydrazine reacts with the starting chloramine to form ammonium chloride and nitrogen. In order to avoid an undesirably high rate of hydrazine decomposition by this undesirable side reaction, the process must be carried out at high temperatures (about 130° C.) and with a large excess of ammonia (20:1 to 30:1) to minimize the reaction of hydrazine product with chloramine reactant. The desired hydrazine product is produced in relatively low concentration (generally from 1% to 3%) in the final reaction mixture, which contains a considerable amount of water, making recovery of anhydrous hydrazine from the mixture rather costly.

The Olin process (Kobe et al., Advances in Petroleum Chemistry and Refining, Vol. 2, Interscience Pub. Inc., New York, N.Y., 1959, Chapter 9) is a modification of the Raschig process employing anhydrous ammonia, which is injected under pressure into an aqueous chloramine solution. Due to the heat of dilution, the temperature of the reaction mixture is raised to about 130° C., the optimum temperature for the reaction of ammonia with chloramine. However, additional heat must be provided from an outside fuel source to carry the reaction to completion and to separate the relatively small concentration of hydrazine from the rather large volume of ammonia in subsequent distillation steps. Further energy is required to remove sodium chloride and sodium hydroxide by-products and to recover the hydrazine. As in the Raschig process, the hydrazine is recovered as the monohydrate. To obtain the pure anhydrous product substantial additional energy is required to drive off the chemically bound water.

The Schestakoff method is based on the degradation of urea by sodium hypochlorite to produce hydrazine. The reaction is analogous to the Hoffmann preparation of primary amines from amides. In the process, a cold aqueous solution of urea and sodium hydroxide is added to a cold aqueous solution of sodium hypochlorite. The heat of reaction increases the temperature to 100° C. at which the reaction takes place at a relatively fast rate. Large quantities of steam must be used in the preparation of the urea solution (43% solution) to offset the huge endotherm of solution. The product, as in the aforementioned commercial processes, is hydrazine monohydrate in rather low concentration (about 3%). Additional energy is required to concentrate, convert the hydrate and fractionate the final hydrazine product. Excessive quantities of alkali and alkali salts are produced as by-products (ratio about 12:1 of by-products to $N_2H_4$ thus manufactured, by weight), which are not reusable in the process.

The Bergbau or Bayer process is yet another commercial procedure for the production of hydrazine. The energy requirements of the Bergbau process are not as great as in the above-described commercial processes. In this process, ammonia is reacted with chlorine in the presence of a ketone to form an intermediate diazocyclopropane or ketazine. The intermediate is then hydrolyzed to the hydrazine hydrate and the latter converted to the desired anhydrous product. The energy requirements for recovery of the hydrazine are approximately the same as for the commercial processes previously described, which involve recovery from aqueous reaction mixtures.

It can thus be seen that the most well known and widely practiced hydrazine manufacturing processes produce a hydrate of hydrazine, which requires substantial energy for recovery of the anhydrous product.

In view of constantly rising energy costs, it is of paramount importance to minimize the use of energy in excess of thermodynamic requirements needed to complete a given reaction. In considering the overall energy requirements of any chemical manufacturing process, the energy needed for the production of raw materials and auxiliary chemicals must also be taken into account. Thus, in the case of hydrazine, the energy requirement for providing $NH_3$, $Cl_2$, NaOCl, urea, NaOH etc., is a significant factor in determining the degree of gain or loss in the energy required to make the final product. Similarly, the weight ratio of by-products versus the desired end-product must be evaluated as another important factor in the overall efficiency of a process. Considered in this light, the above-described prior art methods for the production of hydrazine are decidedly inefficient, especially when it is considered that fifty-eight kcal./mole of product hydrazine are lost from the system upon the formation of hydrazine hydrate.

A process currently used for the commercial production of UDHM involves nitrosation of the sulfuric acid salt of dimethylamine using sodium nitrite to obtain dimethylnitrosamine, which is reduced to the desired product. In addition to suffering from many of the inefficiencies noted above with respect to the hydrazine processes, the dimethylnitrosamine produced as an intermedate in this process is a known carcinogen and poses a potential hazard not only to personnel operating the process but to the environment as well. Because of this potential hazard, the Occupational Safety and Health Administration (OSHA) has implemented strict rules regulating manufacturing processes in which any nitrosamine is used or produced.

Many of the inefficiencies and the hazards inherent in the prior art have been overcome by the process described in my U.S. Pat. No. 4,286,108, which produces hydrazine and hydrocarbyl-substituted hydrazines by reacting a tertiary hydrazinium halide with a compound selected from the group consisting of an alkali metal amide an alkaline earth metal amide, a hydrocarbyl-substituted alkali metal amide or a hydrocarbyl-substituted alkaline earth metal amide, in the presence of a non aqueous inert carrier.

One of the reactants used in the preparation of the tertiary hydrazinium halide according to the process of the '108 patent is chloramine produced by reacting ammonia gas with chlorine. A by-product of this reaction is ammonium chloride which has a tendency to clog the reactant delivery lines, and generally hampers operation of the process.

SUMMARY OF THE INVENTION

In accordance with the present invention, there is provided an improved process for preparing anhydrous hydrazine and its hydrocarbyl-substituted derivatives, which comprises reacting an alkali metal amide, an alkaline earth metal amide, a hydrocarbyl-substituted alkali metal amide, a hydrocarbyl-substituted alkaline earth metal amide, ammonia, or a primary or secondary amine with a chlorinating agent effective to produce chloramine or a hydrocarbyl-substituted chloramine without co-production of an amine hydrochloride; reacting the chloramine thus produced with a tertiary amine to produce a tertiary hydrazinium chloride; and reacting the tertiary hydrazinium chloride with an alkali metal amide, an alkaline earth metal amide, a hydrocarbyl-substituted alkali metal amide or a hydrocarbyl-substituted alkaline earth metal amide under substantially anhydrous conditions to produce the desired product.

The term "hydrocarbyl" as used herein is intended to signify any monovalent radical obtained upon removal of a hydrogen atom from a parent hydrocarbon. Representative of hydrocarbyl radicals are alkyl of 1 to 25 carbon atoms, inclusive such as methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, tetracosyl, pentacosyl and the isomeric forms thereof aryl of 6 to 25 carbon atoms inclusive, such as phenyl, tolyl, xylyl, napthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclohexyl, cycloheptyl, cyclooctyl and the like.

The term "alkali metal", as used herein in, is intended to include lithium, sodium, potassium, rubidium and cesium.

The term "alkaline earth metal", as used herein, is intended to include magnesium, calcium, barium and strontium.

The expression "non-aqueous, reaction medium", as used herein, is intended to signify a liquid solvent or a liquid or solid carrier vehicle for the reactants employed herein, which does not adversely affect the desired course of the reaction and which is substantially free of water. By "substantially free of water" is meant containing less than one weight percent water, preferably less than 0.1%. Illustrative of such carriers are dried kerosene (preferably of low sulfur content and freshly distilled), trialkylamines, such as tripropylamine and tributylamine, carbon tetrachloride, alkyl ethers, and mixtures thereof. It has been found that the use of kerosene as the reaction medium in each step of the process markedly enhances the yield of hydrazine, or hydrocarbyl-substituted hydrazines.

In a preferred embodiment of the present invention there is provided a process for the preparation of anhydrous hydrazine, having very favorable thermodynamics. In this preferred process, chlorine is reacted with an alkali metal amide, such as sodamide or lithium amide to produce chloramine and the corresponding alkali metal salt. The chloramine thus produced undergoes reaction with a tertiary amine to form a tertiary hydrazinium chloride, which is reacted, in turn, with an alkali metal amide to produce anhydrous hydrazine.

All of the by-products of this preferred embodiment are commercially useful substances which may be conveniently recovered. Most of these substances may be recirculated to provide starting materials for certain steps in the process, or to serve as raw materials for the production of said starting materials.

As will be apparent from the following detailed description, the process of the present invention has all of the advantages of my earlier invention covered by U.S. Pat. No. 4,286,108, in that the process requires no specialized equipment, the cost of reactants is minimized and the desired product is readily obtained using standard recovery techniques. In addition, anhydrous hydrazine and hydrocarbyl-substituted hydrazines may be obtained in relatively high concentrations (on the order of 25% to 50%) in the reaction mixture. Another distinct advantage of the process of the present invention is that it avoids the co-production of amine hydrochloride salts which may interfere with the efficient operation of the process.

Another notable advantage of the present invention is that it provides a relatively safe procedure for the preparation of hydrocarbyl-substituted hydrazines, especially UDMH. Unlike the methods currently in practice for producing such products, the process of the present invention is carried out under conditions which offer little or no threat of harm to operating personnel or the environment.

DETAILED DESCRIPTION OF THE INVENTION

The process of the present invention is carried out according to the following general reaction scheme:

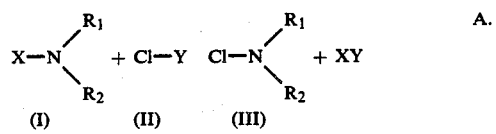

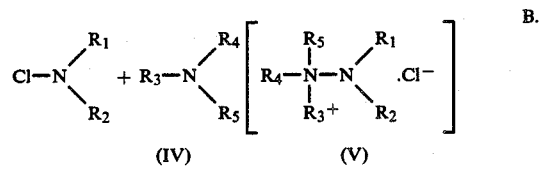

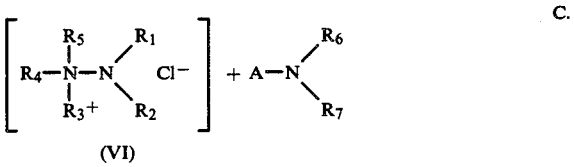

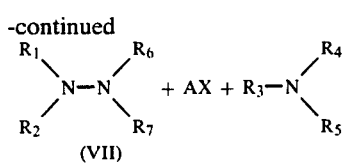

wherein X represents hydrogen, an alkali metal or an alkaline earth metal; $R_1$ and $R_2$ may be the same or different and represent hydrogen or hydrocarbyl radicals; Y represents the residue of a chlorinating agent; $R_3$, $R_4$ and $R_5$ may be the same or different and represent hydrocarbyl radicals; A represents an alkali metal or an alkaline earth metal; and $R_6$ and $R_7$ may be the same or different and represent hydrogen or hydrocarbyl radicals.

In carrying out the reaction to form chloramine, (reaction A), a compound of formula I, which may, for example, be an alkali metal amide, an alkaline earth metal amide, ammonia, or a primary or secondary amine is reacted with a chlorinating agent of formula II. The formula I reactants are well known, as is their preparation. The chlorinating agent used in this reaction is selected from chlorine, hypochlorous acid and chlorine monoxide. The latter two chlorinating agents are conveniently prepared from alkali metal hypochlorites or alkaline earth metal hypochlorites. Details of the preparation are set forth in the examples hereinbelow. The use of these two chlorinating agents in the preparation of hydrocarbyl-substituted chloramines while avoiding co-production of amine hydrochloride salts is considered a particularly significant and innovative aspect of the present invention.

It will be appreciated from the foregoing brief description of the present process that reactions to form chloramine which result in co-production of amine hydrochlorides, such as ammonium chloride, e.g. by the reaction of chlorine with ammonia, are not within the scope of this invention. In general, when chlorine is used as the chlorinating agent in this process, it is desirable to employ an alkali metal amide or an alkaline earth metal amide as the compound of formula I in order to prevent co-production of amine hydrochlorides.

The reaction of hypochlorous acid or chlorine monoxide with mono- and dihydrocarbyl-substituted amines produces the corresponding mono- and dihydrocarbyl-substituted chloramines in good yields. The reaction of these same chlorinating agents with hydrocarbyl-substituted alkali metal amides or hydrocarbyl-substituted alkaline earth metal amides, by contrast, is not as effective a way of producing hydrocarbyl-substituted chloramines. This is primarily due to difficulty in obtaining hydrocarbyl-substituted alkali metals and hydrocarbyl-substituted alkaline earth metal amides. Accordingly, it is preferable to react hypochlorous acid or chlorine monoxide with a hydrocarbyl-substituted amine when a hydrocarbyl-substituted chloramine is desired.

The proportions of reactants of formulae I and II employed in the chloramine reaction is not critical and may vary over a wide range. The stoichiometry of the reaction requires one mole of the formula I compound per mole of the formula II compound. A slight molar excess of the chlorinating agent of formula II present in the reaction mixture may be advantageous.

The chloramine reaction is preferably carried out in an inert, non-aqueous reaction medium. The relative proportion of the reaction medium to the reactants is not critical. In general, the proportion of the reaction medium is from about 25 to about 500 percent by weight of the reactants of the formulae I and II. It is preferred that the reaction medium be miscible with the product chloramine and the tertiary amine with which the chloramine is to be reacted in the following process step, but immiscible with water, so that the product chloramine is easily separable from any water produced as a by-product of the reaction, and may be used without further work-up in the following step, i.e. the preparation of the tertiary hydrazinium chloride.

The reaction to form chloramine may be carried out over a wide range of temperatures, e.g. from about $-10°$ C. to 150° C., and at atmospheric, subatmospheric or superatmospheric pressure. The reaction is most conveniently carried out at room temperature and atmospheric pressure. Upon completion of the reaction, the pressure may be reduced to remove any unreacted volatile materials from the reaction vessel.

The order of addition of reactants is not critical. Satisfactory results have been obtained by placing the compound of formula I into a reaction vessel containing the non-aqueous, inert reaction medium and thereafter adding the chlorinating agent.

Generally, the reaction is completed within 30 to 60 minutes. Of course, the amounts of reactants employed will have an effect on the reaction time. Progress of the reaction may be monitored by employing conventional analytical instruments to determine the disappearance of reactants and the appearance of chloramine (formula III). Upon completion of the reaction, the chloramine may be separated from any water or water-miscible by-product by conventional techniques such as distillation, decantation, freezing or by use of a precipitating agent.

The chloramine thus produced is reacted with a tertiary amine of formula IV to produce a tertiary hydrazinium chloride of formula V (reaction B), according to the procedure of Sisler et al, Inorganic Syntheses, Vol. V, pp. 91–95. In this reaction, the chloramine is introduced into a slight excess of tertiary amine, e.g. trimethyl-, triethyl- or tripropylamine maintained at a temperature of about $-20°$ C. to $-40°$ C. As the reactants are mixed together, crystallization of the tertiary hydrazinium chloride begins to occur. The reaction goes to completion in about 30 to 60 minutes. The reaction mixture is then allowed to warm to room temperature, washed with a suitable solvent (e.g. kerosene) to remove any residual tertiary amine, filtered and dried. The yield of tertiary-hydrazinium salt is quantitative and the overall yield for the first two steps of the reaction scheme is about 65% or better, based on the amount of the formula I compound.

Tertiary hydrazinium chlorides, such as trimethylhydrazinium chloride, tripropylhydrazinium chloride, tri-n-heptylhydrazinium chloride, dimethylphenylhydrazinium chloride, dimethyl-p-tolylhydrazinium chloride, cyclohexyldiethylhydrazinium chloride tripropylmonomethylhydrazinium chloride, and tripropyldimethylhydrazinium chloride are readily prepared using the procedure of Sisler et al.

The reactions to form chloramine and tertiary hydrazinium chloride may be carried out step-wise or simultaneously in a common reaction vessel.

The preparation of anhydrous hydrazine or hydrocarbyl-substituted hydrazine by reacting the tertiary hydrazinium chloride thus produced with an alkali metal amide, an alkaline earth metal amide, a hydrocarbyl-substituted alkali metal amide or a hydrocarbyl-substituted alkaline earth metal amide in the presence of a non-aqueous reaction medium (reaction C) is set forth in detail in my aforementioned U.S. Pat. No. 4,286,108, the entire disclosure of which is incorporated herein by reference, as if written out in full herein.

If desired, mixtures of hydrocarbyl-substituted hydrazines, such as a mixture of monomethylhydrazine and dimethylhydrazine, may be prepared in a common reaction and separated by techniques well known in the art, e.g. fractional distillation. This may be accomplished by chlorinating a mixture of mono- and dimethylamine to form a mixture of mono- and dimethylchloramine, which is thereafter reacted with a tertiary amine and a compound selected from an alkali metal amide, an alkaline earth metal amide, a hydrocarbyl-substituted alkali metal amide, or a hydrocarbyl-substituted alkaline earth metal amide, in succession, to produce the desired mixture of products.

As those skilled in the art will recognize, the process of the present invention may be carried out batch-wise, or, preferably, as a continuous process.

The following examples describe the manner and process of making and using the invention and set forth the best mode contemplated by the inventor for carrying out the invention, but are not to be construed as limiting the invention.

A. Preparation of Chloramine

EXAMPLE 1

A 1000 ml. water-jacketed round-bottom reaction vessel was fitted with an addition funnel and an efficient condenser set downward for distillation by means of a connecting tube. The condenser was attached to a 500 ml. round-bottom receiver vessel, cooled to $-78°$ C. in a dry ice-acetone bath (for convenience in performing the process on a laboratory scale). The receiver was connected, through traps and a manometer, to a water aspirator capable of maintaining a pressure of approximately 25 Torr. in the reaction vessel. Water at approximately 4° C. was circulated from a constant temperature unit through the condenser.

Two hundred milliliters of ethyl ether was placed in the receiver and allowed to cool to $-78°$ C. Approximately 325 grams of ice, 0.48 mole of monomethylamine (37.2 grams of a 40% aqueous solution of monomethylamine obtained from Aldrich Chemical Co.), and 0.49 mole of sodium hypochlorite (375 ml of a 1.325 M sodium hypochlorite solution obtained from Kuehn Chemical Co.) were added to the jacketed reaction vessel to provide equimolar amounts of the reactants. The reaction vessel was closed and the pressure was immediately lowered to 25 Torr. As soon as the initial gas evolution had ceased, the temperature of the water circulating in the reaction vessel jacket was increased to 40°–45° C. Methylchloramine was collected in the distillation receiver for approximately 1 hour. The receiver was then disconnected and the ether solution was decanted into a separate flask containing anhydrous sodium sulfate as a drying agent.

In the distillation of the product methylchloramine a considerable quantity of water is co-distilled and appears as ice in the receiver. Approximately 70 ml. of ether was added to the ice remaining in the receiver, and warmed until it had completely melted. After all of the ice melted, the ether layers were combined and dried over anhydrous sodium sulfate. The yield of methylchloramine was 68.7%.

The yield of this reaction, as well as the yields of the reactions in Examples 2 to 8 which follow, was arrived at by working backwards from the amount of tertiary hydrazinium salt produced in the subsequent reaction step (reaction B). The determination of the yield assumes that chloramine is quantitatively converted to the tertiary hydrazinium salt, which the literature reports to be the case. With the amount of chloramine being thus determined, the yield was based on the amount of amine reactant used to form the chloramine.

EXAMPLE 2

Dimethylchloramine was prepared by repeating the procedure of Example 1, but substituting for the monomethylamine 0.48 mole of dimethylamine (54.0 grams of 40% aqueous solution of dimethylamine obtained from Aldrich Chemical Co.). The yield of dimethylchloramine was 65.8%.

EXAMPLE 3

A 100 ml. three-necked reaction vessel was fitted with an efficient mechanical stirrer, a sub-surface gas inlet tube, a distillation vapor thermometer, and a 20 cm. glass condenser set downward for distillation. The condenser was connected to a vacuum adapter which was then connected, in series, to an oil-filled bubbler, a liquid trap containing sulfuric acid, a second oil-filled bubbler, and finally a gas trap cooled to $-78°$ C. with a dry ice-acetone bath. The adapter was attached to a receiver flask cooled in a dry ice-acetone bath.

A slurry composed of 10 gm. of calcium hypochlorite in 50 ml. of kerosene was placed in the reaction flask. Monomethylamine (0.1 mole) entrained in a stream of nitrogen gas was passed into a wash bottle containing methanol through a gas dispersion tube at the bottom of the wash bottle, and fed via the gas inlet tube into the reaction vessel with stirring.

The reaction mixture was heated to about 135° C. and the product methylchloramine was distilled over to the receiver. The yield of methylchloramine was 81.7%.

Three additional runs of this reaction were carried out and produced the following yields at the reaction temperature given: 27.1% (50° C.); 49.2% (72° C.); 78.2% (117° C.). When the absolute temperature is plotted as a function of the percentage yield, and a linear least squares analysis of the data is performed, a correlation coefficient of 0.991 is obtained [from the equation: % yield=(0.674) (Temperature in K.°)-188.7], indicating that the function is quite linear. Thus it is anticipated that raising the reaction temperature above 135° C. will further increase the yield.

EXAMPLE 4

Dimethylchloramine was prepared by repeating the procedure of Example 3, but substituting dimethylamine (0.1 mole) for the monomethylamine. The yield of dimethylchloramine was 81.2%.

Three additional runs of this reaction were carried out and produced the following yields at the reaction temperature given: 28.3% (52° C.); 49.8% (72° C.); 79% (117° C.). When the absolute temperature is plotted as a function of the percentage yield, and a linear least squares analysis of the data is performed, a correlation coefficient of 0.988 is obtained [from the equation: % yield=(0.674) (Temperature in K.°) -188.7], indicating that the function is again quite linear.

Hence, raising the temperature of this reaction further would also be expected to increase the yield.

The chlorinating agent in Examples 3 and 4 is not the calcium hypochlorite, as such, but hypochlorous acid produced by the reaction of the calcium hypochlorite with methanol, which is picked up by the amine while passing through the wash bottle. In a sense, the calcium hypochlorite is "activated" by the methanol, releasing the chlorinating agent required for the reaction. A by-product of this reaction is calcium methylate. The hypochlorous acid chlorinates the monomethyl- or dimethyl amine, as the case may be, forming the corresponding chloramine and water. The water thus formed is effectively removed from the reaction mixture by reacting instantly with the calcium hypochlorite to form calcium hydroxide, which is readily removed from the reaction mixture. In this way, substantially anhydrous substituted chloramines are obtained for further reaction in accordance with the present invention. Other lower alcohols or water may be substituted for methanol in the wash bottle with similar results.

EXAMPLE 5

An attempt was made to prepare methylchloramine by direct reaction between calcium hypochlorite and monomethylamine, i.e., without pretreatment of the calcium hypochlorite with a lower alcohol or water. No methylchloramine was detectable at reaction temperatures of 0° C., 25° C. or 50° C.

Examples 3, 4 and 5, considered, together, demonstrate the importance of pretreating calcium hypochlorite to form hypochlorous acid as the chlorinating agent.

EXAMPLE 6

A round bottom reaction vessel equipped with a reflux condenser and a pair of gas inlet tubes was charged with 100 ml. of a 15% aqueous solution of sodium hypochlorite. The condenser was connected to a T-tube containing carbon tetrachloride, which was connected, in turn, to a one meter glass column provided with an efficient gas dispersion tube at its base. A 10% mixture of monomethylamine in kerosene was placed in the glass column, which was connected to a receiver for collecting the product chloramine.

Carbon dioxide and nitrogen were introduced into the round bottom vessel separately through the gas inlet tubes. Carbon dioxide reacted with sodium hypochlorite to form $Cl_2O$, as the chlorinating agent. The $Cl_2O$ was scavenged by the carbon tetrachloride in the T-tube and then passed through the gas dispersion tube and into the solution of monomethylamine in kerosene in the glass column. The entire column was wrapped with heating tape and the temperature of the solution was raised slightly. Warm methylchloramine was emitted through the top of the column and collected in the receiver. The yield of methylchloramine was 37.2%.

EXAMPLE 7

Dimethylchloramine was prepared by repeating the procedure of Example 6, but substituting dimethylamine for monomethylamine. The yield of dimethylchloramine was 36.6%.

While chlorination of the primary and secondary amines in Examples 6 and 7 produces the corresponding chloramine together with water, the water may be readily removed from the reaction mixture by maintaining the receiver at a sufficiently low temperature to freeze the water as it collects therein, followed by separation from the desired product. Alternatively, the desired product may be collected in a solvent with which it is miscible, but which is immiscible with water, as in Example 1, above. In either case, substantially anhydrous substituted chloramines are obtained for further reaction in accordance with the present invention.

EXAMPLE 8

Chloramine, $ClNH_2$, was prepared by the reaction between ammonia (0.1 mole) and chlorine monoxide in accordance with the procedure described in Example 6, above. The reaction temperature was 53° C. A chloramine yield of 27.2% was obtained.

B. Preparation of Tertiary Hydrazinium Chloride

1. Step-wise Preparation.

EXAMPLE 9

A cold solution containing 57 ml. of tripropylamine in 100 ml. of dry ethyl ether was added to the solution of methylchloramine in ethyl ether produced in Example 1.

The mixture was held at about −20° C. until crystallization of the tertiary hydrazinium salt appeared to be complete. The volume of ether was then substantially reduced to promote further crystallization. After filtration and vacuum desiccation, the yield of dry tripropylmonomethylhydrazinium chloride was approximately 68.7% (determined as the average of fifteen runs), based upon the amount of monomethylamine used to produce the methylchloramine.

EXAMPLE 10

A 1,1,1-tripropyldimethylhydrazinium chloride was produced by repeating the procedure of Example 9, but substituting dimethylchloramine produced in Example 2, for the chloromethylamine. The yield of 1,1,1-tripropyldimethylhydrazinium chloride was 65.8% (determined as the average of sixteen runs) based on the amount of dimethylamine used in preparing the dimethylchloramine.

2. Simultaneous Preparation with Chloramine.

EXAMPLE 11

A gas washing bottle provided with a gas dispersion tube at the bottom was charged with 100 ml. of kerosene, 0.1 mole of sodamide (4.0 grams) and 0.1 mole of tripropylamine (14.4 grams). A 0.1 mole quantity of chlorine gas (7.1 grams) diluted with nitrogen gas was introduced into the reaction mixture through the dispersion tube. The reaction was carried out at 0° C. for 30–40 minutes. Thereafter, the temperature of the reaction mixture was allowed to come to room temperature and the pressure in the reaction vessel was reduced to remove any volatile material. The yield of tripropylhydrazinium chloride which contained some sodium chloride, as well, was 14.8 gms.

C. Preparation of Anhydrous Hydrazine

EXAMPLE 12

The tripropylhydrazinium chloride produced in Example 11 was reacted with sodamide to produce anhydrous hydrazine.

A 100 ml. three-necked reaction vessel was fitted with an efficient mechanical stirrer, an addition funnel, a sub-surface gas inlet tube, a distillation vapor thermometer, and a 20 cm. glass condenser set downward for distillation. The condenser was connected in series, to an oil-filled bubbler, a liquid trap containing sulfuric acid, a second oil-filled bubbler, and finally a gas trap cooled to −78° C. with a dry ice-acetone bath, and attached to a receiver cooled in a dry-ice acetone bath.

Fifty milliliters of kerosene (Fisher Scientific Co.), which was dried by refluxing over sodium metal, and 0.1 mole of sodamide (Fisher Scientific Co.) were heated in the three-necked reaction vessel to 150° C. under a gentle stream of nitrogen gas. Heating was continued until there was no further evolution of ammonia. Approximately 0.1 mole of dry 1,1,1-tripropylhydrazinium chloride was slurried in 20 ml. of dry kerosene and placed in the dropping funnel.

The salt slurry was added to the three-necked reaction vessel during a 10 minute period. A white vapor was noted and the vapor temperature increased to approximately 100° C. during the salt addition. After approximately 7 minutes the formation of white vapor ceased. The reaction vessel temperature was increased to approximately 165° C. and distillation proceeded for approximately 30 minutes.

After distillation, the fraction collected was distilled using a fractionating column, yielding pure anhydrous hydrazine. The yield of anhydrous hydrazine was 39.6% (determined as the average of three runs) based on the initial amount of sodamide used to form the chloramine.

EXAMPLE 13

Monomethylhydrazine was produced by repeating the procedure of Example 12, but substituting 1,1,1-tripropylmethylhydrazinium chloride (produced as per Example 8) for the 1,1,1-tripropylhydrazinium chloride. The yield of monomethylhydrazine was 53.2% (determined as the average yield of fifteen runs) based on the amount of amine used in forming the chloramine.

EXAMPLE 14

UDMH was produced by repeating the procedure of Example 12, but substituting 1,1,1-tripropyldimethylhydrazinium chloride (produced as per Example 10) for the 1,1,1-tripropylhydrazinium chloride. The yield of UDMH was 56.9% (determined as the average of sixteen runs) based on the amount of the amine used in forming the chloramine.

The hydrazine and hydrocarbyl-substituted hydrazines produced in Examples 12 to 14 are readily recovered as anhydrous products, with considerably less distillation than is required in prior art processes.

The products produced in Examples 11, 12 and 13 were identified by boiling point and density measurements, the measured values corresponding closely to those given in the chemistry literature for anhydrous hydrazine (b.p. 113.8° C.; d. 1.004), methylhydrazine (b.p. 87.5° C.; d. 0.874), and UDMH (b.p. 63.9° C.; d. 0.791).

The procedure for producing anhydrous hydrazine described in Examples 11 and 12 produces sodium chloride and tripropylamine as by-products. The tripropylamine is recoverable in almost quantitative yields and may be conveniently recirculated to provide starting material for the tertiary hydrazinium chloride reaction. The sodium chloride may be subjected to electrolysis to produce sodium, which may be reacted with ammonia to provide sodamide (generating one-half a mole of hydrogen as a by-product, which may be recovered), and chlorine, which may be used in the reaction to form chloramine. By proceeding in this manner, the operating cost of the process may be significantly reduced. Indeed, the cost of the alkali metal amide may be viewed, more or less, as a capital expenditure, since it is continuously regenerated in the process. As previously mentioned, the process may be conveniently run using either sodamide or lithium amide.

Furthermore, the overall process for producing anhydrous hydrazine according to the present invention has a most favorable heat balance, producing about 5.0 million kcal./day* (as indicated in the Heats of Reaction table below), which may be used to generate process steam.

| HEATS OF REACTION | |
|---|---|
| $2Na + 2NH_3 \rightarrow 2NaNH_2 + H_2$ | 1,187,500 KCal./day* |
| $Cl_2 + NaNH_2 \rightarrow NaCl + ClNH_2$ | 1,317,188 KCal./day* |
| $ClNH_2 + R_3N \rightarrow R_3NClNH_2$ | 531,250 KCal./day* |
| $R_3NClNH_2 + NH_2 + NaNH_2 \rightarrow R_3N + NaCl + N_2H_4$ | 2,045,312 KCal./day* |

*Values based on an assumed production of 1000 kg. of anhydrous hydrazine per day, the heat of solution of anhydrous hydrazine in water, as a result of the exothermic formation of $N_2H_4.H_2O$.

Of course, the electrical energy required for production of sodium and chlorine must be considered in determining the overall efficiency of the process, but this requirement can be offset by the energy available from the combustion of the hydrogen generated during the formation of the alkali metal amide.

Although the above examples relating to the preparation of hydrocarbyl-substituted hydrazines are directed to the preparation of alkyl-substituted hydrazines, the same general procedure may be followed for the preparation of aryl-, aralkyl- and cycloalkyl-substituted hydrazines. For example, the sodium derivatives of aniline, benzylamine or cyclohexylamine may be prepared and reacted with an appropriate tertiary-hydrazinium salt to produce the corresponding hydrocarbyl-substituted product, i.e., phenylhydrazine etc., as described in my U.S. Pat. No. 4,286,108.

While certain preferred embodiments of the present invention have been described hereinabove, it is not intended to limit the invention to such embodiments, but various modifications may be made therein and thereto without departing from the spirit and scope of the invention as set forth in the following claims.

What is claimed is:

1. A process for the preparation of a hydrocarbyl-substituted chloramine of the formula $ClNR_1R_2$, wherein $R_1$ is hydrocarbyl and $R_2$ is selected from hydrogen and hydrocarbyl, by reacting chlorine monoxide, produced by reacting an alkali metal hypochlorite or an alkaline earth metal hypochlorite with carbon dioxide, with a primary or secondary amine of the formula $NHR_1R_2$, wherein $R_1$ and $R_2$ are as defined above, the reaction being carried out in a non-aqueous reaction medium and without co-production of an amine hydrochloride salt.

2. A process as claimed in claim 1, wherein the chlorinating agent is prepared by reacting sodium hypochlorite with carbon dioxide.

3. A process as claimed in claim 2, wherein the hydrocarbyl-substituted chloramine product is substantially anhydrous.

* * * * *